(12) United States Patent
Kinnunen et al.

(10) Patent No.: US 8,093,058 B2
(45) Date of Patent: Jan. 10, 2012

(54) METHOD OF PREDICTING PHOSPOLIPIDOSIS INDUCING PROPERTIES OF A SUBSTANCE

(75) Inventors: Paavo Kinnunen, Espoo (FI); Juha-Matti Alakoskela, Helsinki (FI)

(73) Assignee: Paavo Kinnunen, Espoo (FI)

( * ) Notice: Subject to any disclaimer, the term of this patent is extended or adjusted under 35 U.S.C. 154(b) by 255 days.

(21) Appl. No.: 12/517,880

(22) PCT Filed: Dec. 4, 2007

(86) PCT No.: PCT/FI2007/050657
§ 371 (c)(1),
(2), (4) Date: Jun. 22, 2009

(87) PCT Pub. No.: WO2008/068383
PCT Pub. Date: Jun. 12, 2008

(65) Prior Publication Data
US 2010/0323451 A1 Dec. 23, 2010

(30) Foreign Application Priority Data
Dec. 5, 2006 (FI) .................................. 20065774

(51) Int. Cl.
*G01N 33/92* (2006.01)
(52) U.S. Cl. .......................................... 436/71; 424/9.2
(58) Field of Classification Search .................... 436/71, 436/145; 424/9.2
See application file for complete search history.

(56) References Cited

U.S. PATENT DOCUMENTS

| | | | |
|---|---|---|---|
| 7,399,638 B2 * | 7/2008 | Horinouchi et al. | 436/71 |
| 2007/0202487 A1 * | 8/2007 | Fan | 435/4 |
| 2010/0093004 A1 * | 4/2010 | Patton et al. | 435/7.24 |
| 2010/0129790 A1 * | 5/2010 | Sawada et al. | 435/6 |
| 2010/0267061 A1 * | 10/2010 | Hsieh et al. | 435/7.92 |

FOREIGN PATENT DOCUMENTS

| | | |
|---|---|---|
| EP | 1 710 585 A1 | 10/2006 |
| WO | WO 03/010330 A2 | 2/2003 |

OTHER PUBLICATIONS

Vitovic et al. Journal of Medical Chemistry, vol. 51, 2008, pp. 1842-1848.*

H. Fischer, et al; "Prediction of in vitro phospholipidosis of drugs by means of their amphiphilic properties;" Rational Approaches to Drug Design, Proceeedings of the European Symposium on Quantitavie Structure-Activity Relationships; 13th; Duesseldorf, Germany; Aug. 27-Sep. 1, 2000; pp. 286-289; Abstract STN CAPLUS Acc. No. 2002:46502.
H. Fischer, et al.; "Blood-Brain Barrier Permeation: Molecular Parameters Governing Passive Diffusion;" The Journal of Membrane Biology; 1998; vol. 165; pp. 201-211.
P. Suomalainen, et al; "Surface Activity Profiling of Drugs Applied to the Prediction of Blood-Brain Barrier Permeability;" Journal of Medicinal Chemistry; 2004; vol. 47; No. 7; pp. 1783-1788.
J-P. H.T.M. Ploemen, et al; "Use of physicochemical calculation of pKa and CLogP to predict phospholipidosis-inducing potential;" Experimental and Toxicologic Pathology; 2004; vol. 55; pp. 347-355.
S. Schreier, et al.; "Surface active drugs: self-assoccation and interaction with membranes and surfactants;" Physicochemical and biological aspects; Blochimica et Biophysica Acta; 2000; vol. 1508; pp. 210-234.
H. Lullmann, et al; "The Binding of Drugs to Different Polar Lipids In Vitro;" Biochemical Pharmacology; 1979; vol. 28; pp. 3409-3415.
Z.-G. Cui, et al.; "Interfacial and micellar properties of some anionic/cationic binary surfactant systems. 1. Surface properties and prediction of surface tension;" Colloid Polymer Science; 2000; vol. 278; pp. 22-29.
M. P. Mingeot-Leclercq, et al.; "Ultrastructural, physico-chemical and conformation study of the interactions of gentamicin and bis(beta-diethylaminoethylether) hexestrol with negatively-charged phospholipid layers;" Biochemical pharmacology; Mar. 1, 1989; vol. 38; No. 5; pp. 729-741; Abstract Tiivistelma Medline NLM2539158.
International Search Report for International Application No. PCT/FI2007/050657 dated Feb. 19, 2008.
Pavol Vitovič et al.; "Assessment of Drug-Lipid Complex Formation by a High-Throughput Langmuir-Balance and correlation to Phospholipidosis"; *J. Med. Chem.*; 2008; 51; pp. 1842-1848.

* cited by examiner

*Primary Examiner* — Maureen Wallenhorst
(74) *Attorney, Agent, or Firm* — Kratz, Quintos & Hanson, LLP

(57) ABSTRACT

The present invention is directed to a method for predicting the risk of a substance exhibiting phospholipidosis inducing properties, the method including adding the substance to an anionic surfactant to form a mixture of the substance and the surfactant, and determining the effect of the substance on the critical micelle concentration (CMC) of the anionic surfactant by determining the CMC of the mixture, whereby a decrease in the CMC as compared to the CMC of the surfactant prior to the addition of the substance is indicative of a risk of the substance exhibiting phospholipidosis inducing properties.

21 Claims, 3 Drawing Sheets

METHOD OF PREDICTING PHOSPOLIPIDOSIS INDUCING PROPERTIES OF A SUBSTANCE

FIELD OF THE INVENTION

The present invention relates to the determination of ADME-tox properties of substances, such as pharmaceutical compounds, or drugs, or pharmaceutical or food additives, hereafter in the specification at times collectively referred to but not limited to drugs. Specifically, the object of the invention is a method for predicting the phospholipidosis inducing or phospholipidogenic properties (accumulation of phospholipids in the cells) of drugs, i.e. drug-induced phospholipidosis.

Compounds that are most likely to cause phospholipidosis are cationic and amphiphilic, often called CADs (cationic amphiphilic drugs). The current view of the mechanistic basis of phospholipidosis is that these drugs form complexes with phospholipids, thus inhibiting the functioning of phospholipid-degrading enzymes, and leading to accumulation of phospholipids in the lysosomes because of both impaired degradation as well as augmented synthesis. For this reason there is a need for a method to assess the lipid binding of potentially useful compounds. The present invention is aimed at evaluating the interactions of substances, typically drugs, with anionic surfactants, advantageously phospholipids, by assessing the effect of an added substance on the surface activity properties of the surfactant, particularly on the critical micellar concentration (CMC).

BACKGROUND OF THE INVENTION

There are several techniques to determine CMC, e.g. fluorescence assays, light scattering, ultrasound absorption, conductivity, contact angle and surface tension or surface pressure measurements. The hydrophobocity of compounds is commonly determined by measuring their partition coefficient (log P) in an octanol/water two-phase system. Amphiphilicity and detergency properties have conventionally been determined by measuring the effect of the substance on the surface tension of water.

Phospholipidosis (PLD) is a known side effect caused by some pharmaceutical components and drugs. Phospholipids are accumulated in the cells, e.g. in the lungs, kidneys and the liver. Large amounts accumulated in the tissue compromise its normal, physiological function. Especially when a drug is taken for a long period of time the problem is enhanced, since greater amounts of phospholipids may accumulate in the cells. This can in turn lead to chronic, irreversible phospholipidosis and organ failure. This is a serious and expensive problem for the pharmaceutical industry, in particular if becoming evident after the launch of the drug so it has to be drawn back from the market.

Today there are two common ways of testing if a drug is causing PLD. One is to use cell cultures and a method to detect drug-induced changes in the cells. A disadvantage to this method, in addition to being labor-intensive, is that the reproducibility, particularly the between-laboratory reproducibility, in these assays tends to be poor. Likewise, cell cultures need constant care, and are susceptible to infections, variations in the growth conditions, and instabilities in cell lines due to genetic selection in extended culture.

The other option is to use animal tests. Both above methods are expensive and they can thus only be used late in the development process of the drug and neither is suited for large-scale screening of new drug compounds such as performed in lead optimization, for instance. There is thus a need for a test that reveals possible PLD inducing properties early in the development process, as the costs for developing a new drug rise exponentially towards the end of product development pipeline. Such a test would save both money and time in drug development as it would allow for the recognition and possible exclusion of potentially PLD causing compounds. Further this information can also be used for the improvement of compound chemistry so as to reduce its PLD inducing potential by proper adjustment of the compound physicochemistry.

SUMMARY OF THE INVENTION

The present invention is directed to a method for predicting the risk of a substance exhibiting phospholipidosis inducing properties, the method comprising adding the said substance to an anionic surfactant to provide a mixture of substance and surfactant, and determining the effect of said substance on the critical micelle concentration (CMC) of the anionic surfactant by determining the CMC of the mixture, whereby a decrease in the CMC of the mixture as compared to the CMC of the surfactant prior to the addition of the substance is indicative of a risk of said substance exhibiting phospholipidosis inducing properties.

According to the invention the method includes on the one hand the possibility of comparing the CMC of the mixture of substance and surfactant to the CMC of pure surfactant, whereby a decrease in the CMC as compared to pure surfactant is indicative of a risk of said substance exhibiting phospholipidosis inducing properties. According to an embodiment, the invention also includes the possibility of comparing the CMC of the said mixture of substance and surfactant to the CMC of a second mixture of substance and surfactant having a different concentration of substance in the surfactant, whereby a decrease in the CMC of a mixture of substance and surfactant as a result of an increase of the concentration of the substance in the mixture, is indicative of a risk of said substance exhibiting phospholipidosis inducing properties. Thus if the concentration of substance in the second mixture is less than in the said mixture, a decrease in the CMC of the said mixture as compared to the CMC of the second mixture is indicative of a risk of said substance exhibiting phopholipidosis inducing properties.

This latter possibility naturally also means that an increase in the CMC of a mixture of substance and surfactant as a result of a decrease of the concentration of the substance in the mixture, is indicative of a risk of said substance exhibiting phospholipidosis inducing properties.

The method according to the invention thus generally comprises a step of increasing the concentration of the substance in an anionic surfactant, and determining the effect of said substance on the critical micelle concentration (CMC) of the anionic surfactant by determining the CMC of the mixture of substance and surfactant, whereby a decrease in the CMC of the mixture as compared to the CMC of the surfactant prior to the increase of the concentration of the said substance in the said surfactant, is indicative of a risk of said substance exhibiting phospholipidosis inducing properties.

Increasing the concentration of substance includes adding the substance to pure surfactant, that is containing no substance, as well as adding the substance to a mixture of substance and surfactant, in order to increase the concentration of substance in the surfactant.

DETAILED DESCRIPTION OF THE INVENTION

Figure 1:
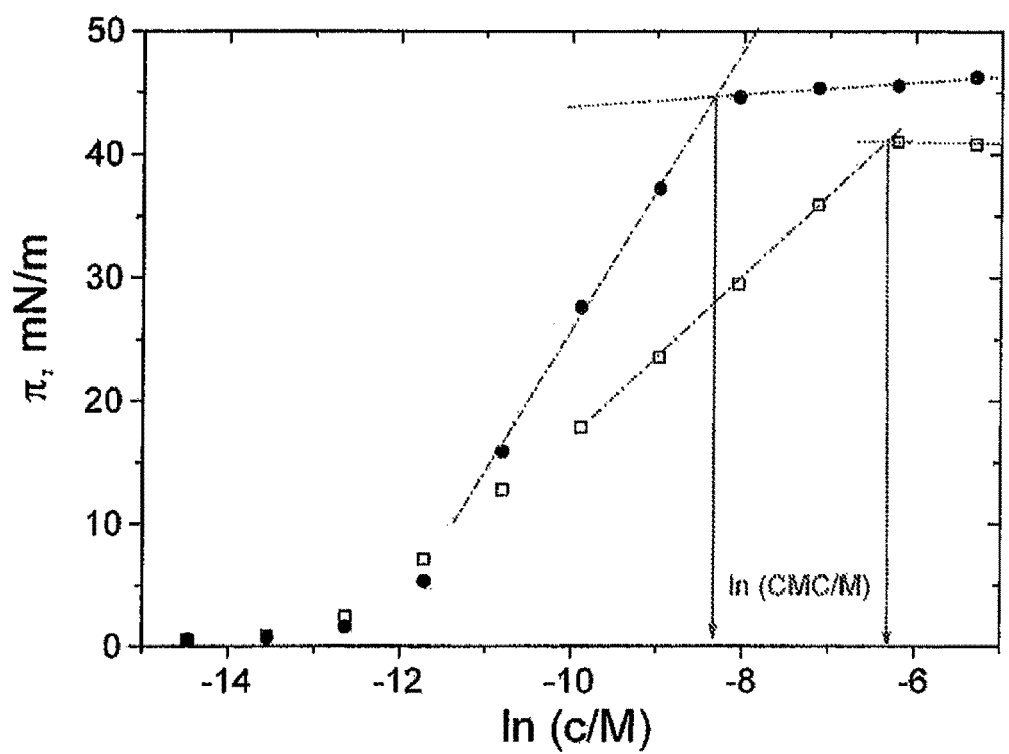
In FIG. 1, two examples of measured surface pressure π vs. natural logarithm of unitless (divided by mol/l) concentration ln (c/M) plots: pure DC8PS (1,2 dioctanoyl-sn-glycero-3-[phosphor-L-serine]) (□) and gentamicin:DC8PS=1:10 (●), are shown. The dash-dot lines and arrows schematically show the principle of obtaining CMC.

When the concentration of a surface-active agent, surfactant, in solution increases, its chemical potential increases. The chemical potential of a compound or substance in a solution (Atkins, P. W., Physical Chemistry, 5th ed., Oxford University Press, 1997) may be seen as a coefficient for the increase of free energy of the system upon a small addition of the compound into the solution. At some concentration the system will reach the point when the chemical potential is sufficient for the formation of surfactant aggregates, typically micelles, and the monomers in excess of this concentration will form aggregates, or micelles, while aggregates are not seen below this concentration. Hence the name critical micelle concentration. After this point a further increase in concentration will no longer significantly increase the concentration of monomers in the solution but only leads to increase in the number of micelles. In mixtures of a surfactant and another compound, which can also be a surfactant, the critical micelle concentration of the mixture is dependent on the free energy of interactions between the two compounds. If the interactions between the surfactant and the other compound are favorable, the mixture will have a lower critical micelle concentration as compared to the surfactant alone, or to a mixture where the concentration of the compound is lower.

Accordingly, the effect of drugs on the CMCs of surfactants reflects the interaction free energy between the drug and the surfactant. This is of interest because the tendency of drugs to form tight complexes with surfactants, such as phospholipids, has been speculated to cause phospholipidosis. The interaction free energy for a drug and a surfactant also describes this tendency for complex formation. Tests depicted above demonstrate that the measurement of the effects of a drug on the CMC of a surfactant provides a good method to predict the phospholipidosis-inducing potency of drugs. However, the phospholipids normally encountered in biological membranes and cells typically have alkyl or acyl chains that are long, i.e. they have several carbon atoms, typically $\geq 14$, in their chains. The CMCs of such long-chain phospholipids are typically within or below nanomolar range and thus too small, for any practical measurement of the kind used here, let alone for high-throughput screening studies. The invention at hand has thus to two aspects: the use of the effect of a drug on the CMC of surfactants to report on the tendency of the drug to form complexes with the surfactants (phospholipids in live cells) and cause phospholipidosis, and the use of surfactants, advantageously short-chain phospholipids. to make these measurements experimentally possible.

According to one embodiment of the invention the method of evaluating the risk of a substance exhibiting phospholipidosis inducing properties further comprises the steps of measuring the surface tension of a solution of said substance in a surfactant at an air-water interface, determining the critical micellar concentration (CMC) from the function of the surface tension vs. the surfactant concentration, such as against the natural logarithm thereof, for at least two different concentrations of said substance in the surfactant, or for at least one concentration of the substance in the surfactant and for pure surfactant.

The method according to the invention also comprises evaluating the substance:surfactant ratio $R_{1/2}$, where the CMC has decreased by 50% of the largest change obtained with increasing substance:surfactant ratio, and comparing the obtained substance:surfactant ratio $R_{1/2}$ to predetermined boundary-limits for $R_{1/2}$; and/or evaluating the minimum CMC for the substance in surfactant and comparing the same to predetermined boundary limits for minimum CMC and, based on the comparisons, classifying the drug in one of at least two risk groups, such groups indicating or classifying the phospholipidosis inducing risk of said substance.

According to the invention the substance/surfactant molar ratio used for determining the effect on the CMC is in the range of 0.0 to 2.0, preferably 0.0 to 1.0 or 0.0 to 0.5, namely starting from pure surfactant (no substance) up to two moles of substance, typically up to 0.5 moles of substance per mole of surfactant.

In a preferred embodiment of the invention the volume of a sample used for determining the CMC can be up to 50 μl and the surfactants concentration up to 5 mM.

According to a preferred embodiment of the invention the effect of the substance on the CMC is determined by determining the CMC for pure surfactant and for a surfactant containing said substance, respectively, for at least one ratio value between substance and surfactant.

According to the invention the risk of a substance having phospholipidosis inducing properties is higher for a substance which has a stronger decreasing effect on the CMC as compared to a substance which has a weaker decreasing effect on the CMC, at the same concentration, and/or also for a substance of which a smaller concentration is sufficient to cause a predetermined decrease in the CMC as compared to a substance of which a higher concentration is needed for causing the same decrease.

According to a preferred embodiment of the invention the anionic surfactant is a phospholipid containing at the most 28 carbon atoms, preferably 10-28 carbon atoms in all the chains combined, often containing from 4 to 12 carbon atoms in a carbon chain. Typical phospholipids for use in this invention are phosphatidylserines, phosphatidylglycerols, phosphatidic acids, phosphatidylinositol and phosphatidylinositol phosphates, and respective lysolipid, peroxylipid, oxylipid, plasmalogen and dialkyl lipid variants of the above, as well as anionic phospholipid analogs and anionic surfactants, such as alkyl- and acylphosphates or -monomethylphosphates or the like, having short enough hydrophobic chains to have CMCs higher than approx. 1 µM.

According to the invention it is also possible to use a mixture of surfactants.

The surface tension or the surface pressure (which is the surface tension of a pure surface—the surface tension of the surface in the presence of the substance) is advantageously measured using mixtures of substance and a surfactant having a molar ratio of drug to surfactant from 0 to 1. Typically at least four to five points are needed for reliable evaluation of $R_{1/2}$.

According to the invention the drug can be dissolved in a suitable solvent, such as DMSO or alcohol.

The surface activity (tension or pressure) measurements can easily and effectively be carried out, for example using well plates having for example different drugs and different concentrations of drugs in the various rows and columns of the well plate.

One usable apparatus for such surface activity measurements is the MultiPi apparatus by Kibron Inc.

Figure 2:
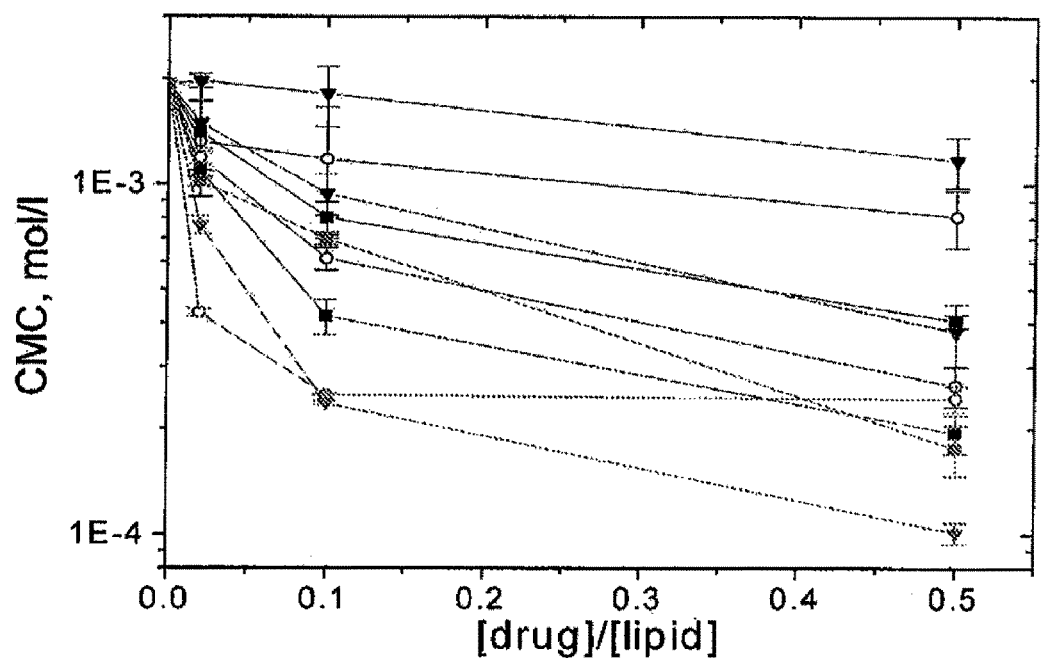
FIG. 2 shows examples of CMC vs. drug:lipid ratio curves. The connecting lines are only to guide the eye. The symbols are as follows: clozapine (■), haloperidol (○), 1-phenylpiperazine (▼), chlorpromazine (■), promazine (○), propranolol (▼), amiodarone (■), gentamicin (○), and perhexyline (▼).

FIG. 1 shows an example of CMC determination using surface pressure measurement. Once the bulk concentration reaches CMC, the surface pressure no longer significantly increases with a further increase in concentration, as this increase in concentration no longer increases the monomer concentration and chemical potential the in bulk. Based on the evaluated CMC values CMC vs. drug:lipid ratio curves can be constructed as those shown in FIG. 2.

According to one embodiment of the invention the cubic interpolation function can be used to obtain $R_{1/2}$ which gives the drug:surfactant ratio where the CMC would have decreased by 50%, that is:

$$CMC = \frac{1}{2}(p+m),$$

wherein p is the CMC obtained in pure surfactant, and m is the minimum CMC determined for the drug in surfactant.

Figure 3:
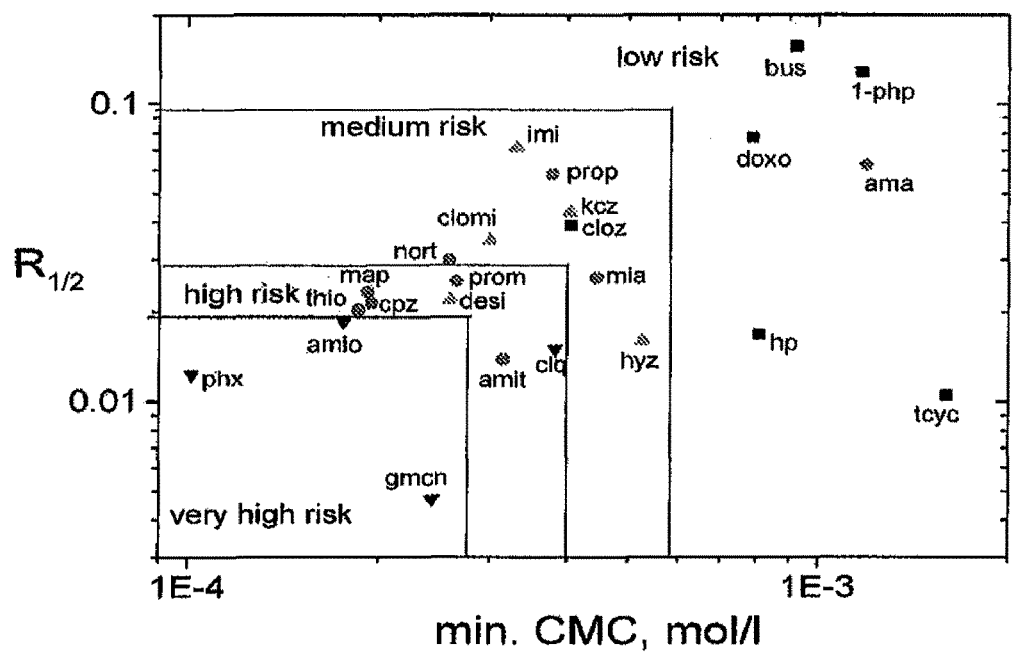
FIG. 3 shows the drug:lipid ratio giving half of the maximal effect on CMC, $R_{1/2}$, vs. minimum of CMC obtained with drug:lipid ratio of up to 1:2. The symbols indicate the classifications to one of the four groups: group 1 (■) with no phospholipidosis potential, group 2 (●) causing phospholipidosis in cultured cells but having low potency to cause phospholipidosis in animals, group 3 (▲) known to cause phospholipidosis in animals, and group 4 (▼), the substances that have caused phospholipidosis in humans (Ploeman, J.-P. H. T. M., J. Kelder, T. Hafmans, H. van de Sandt, J. A. van Burgsteden, P. J. M. Salemink, and E. van Esch (2004) Use of physicochemical calculation of pKa and C Log P to predict phospholipidosis-inducing potential. A case study with structurally related piperazines. *Eur. Toxic. Pathol.*; Morelli, J. K., M. Buehrle, F. Pognan, L. R. Barone, W. Fieles, and P. J. Ciaccio (2006) Validation of an in vitro screen for phospholipidosis using a high-content biology platform. *Cell Biol. Toxicol.*). The abbreviations are as follows: ama=amantadine, amio=amiodarone, amit=amitriptyline, bus=buspirone, clomi=clomipramine, cloz=clozapine, clq=chloroquine, cpz=chlorpromazine, desi=desipramine, doxo=doxorubicin, gmcn=gentamicin, hp=haloperidol, hyz=hydroxyzine, imi=imipramine, kcz=ketoconazole, map=maprotiline, mia=mianserin, nort=nortriptyline, 1-php=1-phenylpiperazine, phx=perhexyline, prom=promazine, prop=propranolol, tcyc=tetracycline, and thio=thioridazine.

With reference to FIG. 3, according to one embodiment of the invention the drug:lipid ratio $R_{1/2}$ for a drug is compared to predetermined boundary-limits for $R_{1/2}$ of four predetermined groups defining different risks of the drug inducing phospholipidosis. Also the minimum CMC for the drug can be determined and compared to corresponding boundary limits for minimum CMC. The said four risk groups can be defined as: group 1 with no phospholipidosis potential, group 2 with low potency to cause phospholipidosis, group 3 as known to cause phospholipidosis in animals and group 4 as known to have caused phospholipidosis in humans. The boundary limits are based on tests made by conventional methods on whether a substance causes phospholipidosis.

The method for evaluating the result of the determination requires some reference data of the phospholipidogenic potency of known set of compounds. Such data could for example be derived from cell or animal experiments. Using the values from such reference data allows to assign the levels of phospholipidosis risk associated to the different values of the test parameters of maximal CMC decrease and $R_{1/2}$ (see FIG. 3). These risk levels assigned based on compounds of known phospholipidogenic potency allows to evaluate the phospholipidogenic potency of unknown compounds.

According to the invention if a drug shows a high $R_{1/2}$ optionally in combination with a high minimum CMC, the drug can be classified as a drug with a low risk of inducing phospholipidosis. On the other hand, a low $R_{1/2}$ and/or a low minimum CMC indicates the drug being one with a high risk of inducing phospholipidosis, as is evident e.g. from FIG. 3.

Tests have shown that the direct measurement of the tendency of compounds to complex formation with a short-chain phospholipid correlates well with the tendency of these compounds to cause phospholipidosis, and is thus potentially useful for the evaluation of the phospholipidosis-inducing potency of unknown compounds.

EXAMPLE

In the example, appropriate amounts of drug powders where weighed and dissolved to give 62.5 mM stock, of which 12.5 mM and 2.5 mM dilutions were made. Stocks were prepared in DMSO, except for gentamicin, which was soluble to water, but not in DMSO, and tamoxifen, which was soluble in neither DMSO nor water, but had to be dissolved in ethanol. The phospholipid 1,2-dioctanoyl-sn-glycero-3 [phospho-L-serine] ($DC_8PS$) was dissolved in chloroform, and the concentration was determined gravimetrically using a high-precision microbalance.

First, to make the phospholipid solution, an appropriate amount of $DC_8PS$ dissolved in chloroform was transferred to a new test tube and evaporated to dryness under a gentle stream of nitrogen. Following this, 20 mM HEPES buffer (pH 7.4) containing 0.1 mM EDTA was added onto the dry lipid to give 5 mM $DC_8PS$ concentration, and sample was rigorously mixed, followed by a 30 minute incubation at 60° C., rigorous mixing, and a second 30 minute incubation at 60° C.

The solutions where then pipetted into a 96-well plate. First, 175 µl of 5 mM $DC_8PS$ solution was added to each well of the first column (column 1) of a 96-well plate (which contains 8 rows and 12 columns). To all the other wells, 105 µl of the HEPES buffer was applied. Following this, 7 µl of a drug stock was added to a well in the first column. The different drug stocks, 62.5 mM, 12.5 mM, and 2.5 mM, gave the drug to phospholipid mole ratios of 1:2, 1:10, and 1:50, respectively. In some cases, also 1:1 mole ratio was measured, and this required adding 14 µl of the drug stock to the first column. Every plate measured contained also one row, where instead of drug only 7 µl of DMSO was added. Thus, each plate contained one row with phospholipid only, and seven rows with different drugs and/or different drug:phospholipid ratios.

A multi channel automatic pipette was used to mixed to contents of the wells in the first column, and then 70 µl of the solutions in the first columns were transferred onto the 105 µl of buffer in the second column. After this, the contents of the wells in the second column were mixed, and 70 µl of the solutions were transferred onto the 105 µl of buffer in the wells of the third column, and this was continued column by column until the eleventh column was reached. This gives approximately 0.4-dilution factor between the subsequent columns. This gives approximately the concentrations (column shown in parentheses) 5.0 mM (1), 2.0 mM (2), 0.80 mM (3), 0.32 mM (4), 0.128 mM (5), 51 µM (6), 20 µM (7), 8.2 µM (8), 3.3 µM (9), 1.3 µM (10), 0.52 µM (11), and 0 (12) of the phospholipid in the different columns. The different rows then contain, for example, only phospholipid in row A, drug 1:phospholipid=1:50 in row B, drug 1:phospholipid=1:10 in row C, drug 1:phospholipid=1:2 in row D, drug 2:phospholipid=1:50 in row E, drug 2:phospholipid=1:10 in row F, drug 2:phospholipid=1:2 in row G, and drug 3:phospholipid=1:50 in row H.

50 µl of solution from each well on the pipeted 96-well plate was transferred to the corresponding well on the Kibron measurement plate, and the partioning was then allowed to stabilize for 10-15 minutes. After this the surface tension in each well was measured using a Kibron Delta-8 multichannel tensiometer, and the critical micellar concentrations were obtained by using the dedicated software to evaluate the concentration at which the minimum in surface tension (the maximum in surface pressure) was reached.

The invention claimed is:

1. A method for predicting the risk of a substance exhibiting phospholipidosis inducing properties, the method comprising adding the said substance to an anionic surfactant to provide a mixture of substance and surfactant, and determining the effect of said substance on the critical micelle concentration (CMC) of the anionic surfactant by determining the CMC of the mixture, whereby a decrease in the CMC of the mixture as compared to the CMC of the surfactant prior to the addition of the substance is indicative of a risk of said substance exhibiting phospholipidosis inducing properties.

2. The method according to claim 1 comprising comparing the CMC of the said mixture of substance and surfactant to the CMC of the mixture prior to the addition of the substance, or comparing the CMC of the said mixture to the CMC of a second mixture of substance and surfactant containing a different concentration of substance,
whereby when the value of CMC is lower in the mixture with the higher concentration of substance present, this is indicative of a risk of said substance exhibiting phospholipidosis inducing properties.

3. The method according to claim 2, wherein the surfactant is a phospholipid.

4. The method according to claim 3, wherein the phospholipid is a phosphati-dylserine, a phosphatidylglycerol, a phosphatidic acid, a phosphatidylinosi-tol or phosphatidylinositolphosphate, or the lysolipid, peroxylipid, oxidized, plasmalogen, or dietherlipid derivative of these phospholipids, or a phospholipid analog, and wherein the phospholipid has a total of less than 28 carbon atoms in all the chains combined.

5. The method according to claim 1, further comprising the steps of:
measuring the surface tension of a solution of said substance in the surfactant at an air-water interface; and
determining the critical micellar concentration (CMC) from the function of the surface tension vs. the surfactant concentration for at least two different concentrations of said substance in the surfactant, or for at least one concentration of the substance in the surfactant and for pure surfactant.

6. The method according to claim 5, wherein the function is a plotted curve.

7. The method according to claim 5, wherein the surfactant is a phospholipid.

8. The method according to claim 7, wherein the phospholipid is a phosphati-dylserine, a phosphatidylglycerol, a phosphatidic acid, a phosphatidylinosi-tol or phosphatidylinositolphosphate, or the lysolipid, peroxylipid, oxidized, plasmalogen, or dietherlipid derivative of these phospholipids, or a phospholipid analog, and wherein the phospholipid has a total of less than 28 carbon atoms in all the chains combined.

9. The method according to claim 1, comprising
determining the substance:surfactant ratio $R_{1/2}$, which is defined as the substance/surfactant ratio when the CMC has value:

$$CMC = \tfrac{1}{2}(p+m),$$

wherein p is the value of CMC obtained with no substance present, and m is the minimum CMC determined with the substance in surfactant;
comparing the obtained substance:surfactant ratio $R_{1/2}$ to predetermined boundary-limits for $R_{1/2}$; and/or determining the minimum CMC for the substance in surfactant and comparing the same to predetermined boundary limits for minimum CMC; and,
based on the comparisons, classifying the substance as being in one of at least two risk groups indicating or classifying the phospholipidosis inducing risk of said substance.

10. The method according to claim 9, wherein four risk groups are used for indicating the phospholipidosis inducing risk of the substance.

11. The method according to claim 10, wherein the four groups are defined as: group 1 with no phospholipidosis potential, group 2 with low potency to cause phospholipidosis, group 3 as known to cause phospholipidosis in animals and group 4 as known to have caused phospholipidosis in humans.

12. The method according to claim 1, wherein the surfactant is a phospholipid.

13. The method according to claim 12, wherein the phospholipid is a phosphati-dylserine, a phosphatidylglycerol, a phosphatidic acid, a phosphatidylinosi-tol or phosphatidylinositolphosphate, or the lysolipid, peroxylipid, oxidized, plasmalogen, or dietherlipid derivative of these phospholipids, or a phospholipid analog, and wherein the phospholipid has a total of less than 28 carbon atoms in all the chains combined.

14. The method according to claim 1, wherein the substance is dissolved in a water-soluble solvent.

15. The method according to claim 14, wherein the water-soluble solvent is DMSO.

16. The method according to claim 1, wherein the substance is an amphiphilic and/or cationic substance.

17. The method according to claim 1, wherein the substance is a pharmaceutical compound.

18. The method according to claim 1, comprising determining the CMC for a substance/surfactant molar ratio in the range of up to 2.0.

19. The method according to claim 18, comprising determining the CMC for a substance/surfactant molar ratio in the range of up to 1.0.

20. The method according to claim 1, wherein the volume of a sample of the mixture used for determining the CMC is up to 50 µl and the surfactant concentration is up to 5 mM.

21. The method according to claim 1, comprising determining the CMC for pure surfactant and for said surfactant containing said substance for at least one substance/surfactant ratio value.

* * * * *